United States Patent
Edelmann et al.

(10) Patent No.: US 8,481,165 B2
(45) Date of Patent: Jul. 9, 2013

(54) AGENT FOR PROVIDING SUBSTRATES BASED ON CELLULOSE AND/OR STARCH WITH WATER REPELLENT AND SIMULTANEOUSLY ANTIFUNGAL, ANTIBACTERIAL INSECT-REPELLENT AND ANTIALGAL PROPERTIES

(75) Inventors: Roland Edelmann, Rheinfelden (DE); Christian Waβmer, Hausen (DE); Peter Jenkner, Rheinfelden (DE); Jaroslaw Monkiewicz, Rheinfelden (DE); Holger Militz, Bovenden (DE); Carsten Mai, Göttingen (DE); Steffen Donath, Gotha (DE)

(73) Assignee: Evonik DeGussa GmbH, Essen (DE)

( * ) Notice: Subject to any disclaimer, the term of this patent is extended or adjusted under 35 U.S.C. 154(b) by 1261 days.

(21) Appl. No.: 11/572,688

(22) PCT Filed: Jun. 3, 2005

(86) PCT No.: PCT/EP2005/052560
§ 371 (c)(1),
(2), (4) Date: Jul. 30, 2007

(87) PCT Pub. No.: WO2006/010667
PCT Pub. Date: Feb. 2, 2006

(65) Prior Publication Data
US 2011/0143147 A1    Jun. 16, 2011

(30) Foreign Application Priority Data
Jul. 29, 2004   (DE) .......................... 10 2004 037 044

(51) Int. Cl.
*B32B 9/02* (2006.01)
*C09D 5/14* (2006.01)
*B05D 3/10* (2006.01)

(52) U.S. Cl.
USPC .............................. 428/447; 106/2; 427/296

(58) Field of Classification Search
None
See application file for complete search history.

(56) References Cited

U.S. PATENT DOCUMENTS

| | | | |
|---|---|---|---|
| 3,730,701 A * | 5/1973 | Isquith et al. | 504/153 |
| 3,794,736 A * | 2/1974 | Abbott et al. | 514/63 |
| 3,865,728 A * | 2/1975 | Abbott et al. | 210/501 |
| 4,282,366 A * | 8/1981 | Eudy | 556/413 |
| 4,386,134 A * | 5/1983 | Puhringer | 428/447 |
| 4,404,239 A * | 9/1983 | Grunewalder | 427/393 |

(Continued)

FOREIGN PATENT DOCUMENTS
EP        0 953 591       11/1999

OTHER PUBLICATIONS

Wood Handbook-Wood as an Engineering Material, Chapter 14, Wood Preservation, Rebecca E. Ibach, 2001, 28 pages.*
U.S. Appl. No. 11/955,215, filed Jan. 10, 2008, Jenkner, et al.

(Continued)

*Primary Examiner* — Robert S Loewe
(74) *Attorney, Agent, or Firm* — Oblon, Spivak, McClelland, Maier & Neustadt, L.L.P.

(57) ABSTRACT

The invention relates to an agent for providing substrates based on cellulose and/or starch with water-repellent and simultaneously antifungal, antibacterial, insect-repellent and antialgal properties, which contains water and, as active substance, at least one linear, cyclic, branched or crosslinked co-oligomer or mixtures of co-oligomers from the series consisting of the alkyl-/aminoalkyl-/alkoxy- or hydroxy-siloxanes, the use of such agents and a special treatment process using such agents.

16 Claims, 5 Drawing Sheets

Sorption behavior on conditioning

U.S. PATENT DOCUMENTS

| | | | |
|---|---|---|---|
| 4,406,892 A * | 9/1983 | Eudy | 514/63 |
| 4,847,088 A * | 7/1989 | Blank | 424/404 |
| 4,913,972 A * | 4/1990 | Grunewalder et al. | 428/425.5 |
| 4,921,701 A * | 5/1990 | Blehm Blank | 424/401 |
| 4,929,498 A * | 5/1990 | Suskind et al. | 442/123 |
| 5,035,892 A * | 7/1991 | Blank et al. | 424/443 |
| 5,051,129 A * | 9/1991 | Cuthbert et al. | 106/2 |
| 5,209,775 A * | 5/1993 | Bank et al. | 106/2 |
| 5,442,011 A * | 8/1995 | Halling | 524/873 |
| 5,591,818 A | 1/1997 | Standke et al. | |
| 5,629,400 A * | 5/1997 | Standke et al. | 528/38 |
| 5,679,147 A | 10/1997 | Standke et al. | |
| 5,786,493 A | 7/1998 | Rauleder et al. | |
| 5,808,125 A | 9/1998 | Standke et al. | |
| 5,849,942 A | 12/1998 | Standke et al. | |
| 5,863,509 A | 1/1999 | Standke et al. | |
| 5,885,341 A * | 3/1999 | Standke et al. | 106/287.11 |
| 5,932,757 A | 8/1999 | Standke et al. | |
| 6,018,011 A | 1/2000 | Scheim et al. | |
| 6,054,601 A | 4/2000 | Standke et al. | |
| 6,093,841 A * | 7/2000 | Winkhofer et al. | 556/425 |
| 6,133,466 A | 10/2000 | Edelmann et al. | |
| 6,176,918 B1 | 1/2001 | Glausch et al. | |
| 6,177,582 B1 | 1/2001 | Jenkner et al. | |
| 6,228,936 B1 | 5/2001 | Standke et al. | |
| 6,239,194 B1 | 5/2001 | Standke et al. | |
| 6,251,989 B1 | 6/2001 | Edelmann et al. | |
| 6,255,513 B1 | 7/2001 | Standke et al. | |
| 6,288,256 B1 | 9/2001 | Standke et al. | |
| 6,361,871 B1 * | 3/2002 | Jenkner et al. | 428/447 |
| 6,395,858 B1 * | 5/2002 | Mack et al. | 528/38 |
| 6,403,228 B1 | 6/2002 | Mack et al. | |
| 6,491,838 B1 | 12/2002 | Standke et al. | |
| 6,500,883 B1 | 12/2002 | Mack et al. | |
| 6,534,667 B1 | 3/2003 | Standke et al. | |
| 6,641,870 B2 | 11/2003 | Bartkowiak et al. | |
| 6,663,683 B2 | 12/2003 | Lortz et al. | |
| 6,676,719 B2 | 1/2004 | Lortz et al. | |
| 6,685,766 B2 | 2/2004 | Standke et al. | |
| 6,689,468 B2 | 2/2004 | Edelmann et al. | |
| 6,695,904 B2 | 2/2004 | Burger et al. | |
| 6,699,586 B2 | 3/2004 | Edelmann et al. | |
| 6,713,186 B1 | 3/2004 | Jenkner et al. | |
| 6,727,375 B2 | 4/2004 | Steding et al. | |
| 6,767,377 B2 | 7/2004 | Schumacher et al. | |
| 6,767,982 B2 | 7/2004 | Standke et al. | |
| 6,770,327 B2 * | 8/2004 | Edelmann et al. | 427/387 |
| 6,773,697 B2 | 8/2004 | Hemme et al. | |
| 6,773,814 B2 | 8/2004 | Schumacher et al. | |
| 6,808,769 B2 | 10/2004 | Batz-Sohn et al. | |
| 6,830,816 B2 | 12/2004 | Mehnert et al. | |
| 6,841,197 B2 | 1/2005 | Standke et al. | |
| 6,905,632 B2 | 6/2005 | Lortz et al. | |
| 6,946,537 B2 | 9/2005 | Krafczyk et al. | |
| 6,991,190 B2 | 1/2006 | Lortz et al. | |
| 7,015,270 B2 | 3/2006 | Scharfe et al. | |
| 7,026,398 B2 | 4/2006 | Monkiewicz et al. | |
| 7,083,769 B2 | 8/2006 | Moerters et al. | |
| 7,244,302 B2 | 7/2007 | Schumacher et al. | |
| 7,255,735 B2 | 8/2007 | Meyer et al. | |
| 7,374,787 B2 | 5/2008 | Lortz et al. | |
| 7,399,487 B2 | 7/2008 | Batz-Sohn et al. | |
| 7,427,442 B2 | 9/2008 | Albert et al. | |
| 7,470,423 B2 | 12/2008 | Lortz et al. | |
| 7,538,142 B2 | 5/2009 | Lortz et al. | |
| 7,572,854 B2 | 8/2009 | Schneider et al. | |
| 7,578,877 B2 | 8/2009 | Giessler et al. | |
| 7,598,409 B2 | 10/2009 | Just et al. | |
| 7,611,753 B2 | 11/2009 | Bartkowiak et al. | |
| 7,615,577 B2 | 11/2009 | Lortz et al. | |
| 7,645,335 B2 | 1/2010 | Lortz et al. | |
| 7,666,257 B2 | 2/2010 | Giessler-Blank et al. | |
| 7,670,422 B2 | 3/2010 | Giessler-Blank et al. | |
| 7,704,561 B2 * | 4/2010 | Mehta et al. | 427/393.4 |
| 7,749,322 B2 | 7/2010 | Schumacher et al. | |
| 7,780,777 B2 | 8/2010 | Perlet et al. | |
| 7,815,936 B2 | 10/2010 | Hasenzahl et al. | |
| 7,834,073 B2 | 11/2010 | Standke et al. | |
| 7,976,719 B2 | 7/2011 | Batz-Sohn et al. | |
| 8,012,367 B2 | 9/2011 | Hasenzahl et al. | |
| 2002/0098243 A1 | 7/2002 | Edelmann et al. | |
| 2002/0127415 A1 | 9/2002 | Standke et al. | |
| 2002/0192385 A1 * | 12/2002 | Jenkner et al. | 427/387 |
| 2002/0197311 A1 | 12/2002 | Hasenzahl et al. | |
| 2003/0018155 A1 | 1/2003 | Krafczyk et al. | |
| 2003/0108580 A1 | 6/2003 | Hasenzahl et al. | |
| 2003/0186066 A1 * | 10/2003 | Monkiewicz et al. | 428/447 |
| 2003/0228271 A1 | 12/2003 | Batz-Sohn et al. | |
| 2004/0240062 A1 | 12/2004 | Lortz et al. | |
| 2005/0096250 A1 * | 5/2005 | Ohlhausen et al. | 510/504 |
| 2005/0169861 A1 | 8/2005 | Lortz et al. | |
| 2005/0265934 A1 | 12/2005 | Schumacher et al. | |
| 2006/0063002 A1 | 3/2006 | Edelmann et al. | |
| 2006/0104881 A1 | 5/2006 | Lortz et al. | |
| 2006/0159635 A1 | 7/2006 | Meyer et al. | |
| 2006/0159636 A1 | 7/2006 | Meyer et al. | |
| 2006/0159637 A1 | 7/2006 | Meyer et al. | |
| 2006/0163533 A1 | 7/2006 | Batz-Sohn et al. | |
| 2006/0229210 A1 | 10/2006 | Neugebauer et al. | |
| 2006/0292192 A1 | 12/2006 | Hasenzahl et al. | |
| 2007/0054056 A1 | 3/2007 | Albert et al. | |
| 2007/0231280 A1 | 10/2007 | Schumacher et al. | |
| 2007/0297998 A1 | 12/2007 | Meyer et al. | |
| 2008/0027161 A1 | 1/2008 | Schlosser et al. | |
| 2008/0095724 A1 | 4/2008 | Hasenzahl et al. | |
| 2008/0187673 A1 | 8/2008 | Standke et al. | |
| 2008/0188617 A1 | 8/2008 | Standke et al. | |
| 2008/0213325 A1 | 9/2008 | Schumacher et al. | |
| 2008/0249237 A1 | 10/2008 | Hager et al. | |
| 2008/0264299 A1 | 10/2008 | Lortz et al. | |
| 2009/0022898 A1 | 1/2009 | Standke et al. | |
| 2009/0047225 A1 | 2/2009 | Hasenzahl et al. | |
| 2009/0069464 A1 | 3/2009 | Standke | |
| 2009/0131694 A1 | 5/2009 | Schumacher et al. | |
| 2009/0186053 A1 | 7/2009 | Meyer et al. | |
| 2009/0261309 A1 | 10/2009 | Lortz et al. | |
| 2010/0117021 A1 | 5/2010 | Batz-Sohn et al. | |
| 2010/0119851 A1 | 5/2010 | Giessler-Blank et al. | |
| 2010/0159144 A1 | 6/2010 | Standke et al. | |
| 2010/0209339 A1 | 8/2010 | Schumacher et al. | |
| 2010/0209719 A1 | 8/2010 | Borup et al. | |
| 2010/0233392 A1 | 9/2010 | Batz-Sohn et al. | |
| 2010/0308287 A1 | 12/2010 | Lortz et al. | |
| 2011/0144226 A1 | 6/2011 | Spyrou et al. | |

OTHER PUBLICATIONS

U.S. Appl. No. 11/995,751, filed Jan. 15, 2008, Edelmann, et al.
U.S. Appl. No. 11/955,550, filed Jan. 14, 2008, Edelmann, et al.
U.S. Appl. No. 12/673,390, filed Feb. 16, 2010, Wassmer, er al.
U.S. Appl. No. 12/674,271, filed Feb. 19, 2010, Albert, et al.
U.S. Appl. No. 12/674,601, filed Feb. 22, 2010, Jenkner, et al.
U.S. Appl. No. 11/572,691, filed Jan. 25, 2007, Edelmann, et al.
U.S. Appl. No. 08/124,955, filed Sep. 21, 1993, Standke, et al.
U.S. Appl. No.10/112,045, filed Apr. 1, 2002, Mehnert, et al.
U.S. Appl. No. 10/563,022, filed Dec. 30, 2005, Edelmann, et al.
U.S. Appl. No. 10/576,467, filed Apr. 20, 2006, Edelmann, et al.
U.S. Appl. No. 11/572,555, filed Jan. 23, 2007, Just, et al.
U.S. Appl. No. 11/576,504, filed Apr. 2, 2007, Mueh, et al.
U.S. Appl. No. 12/159,785, filed Jul. 1, 2008, Standke, et al.
U.S. Appl. No. 12/181,629, filed Sep. 4, 2008, Militz, et al.

* cited by examiner

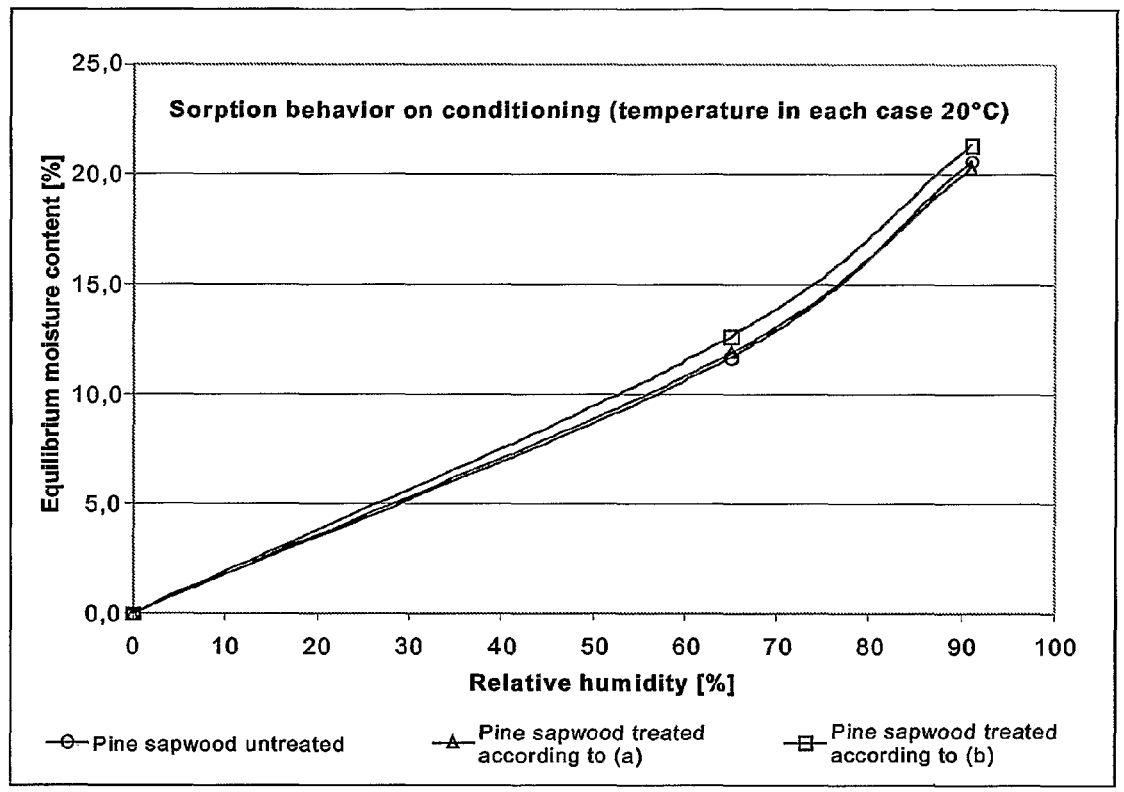
Fig. 1 for example 1: Sorption behavior on conditioning

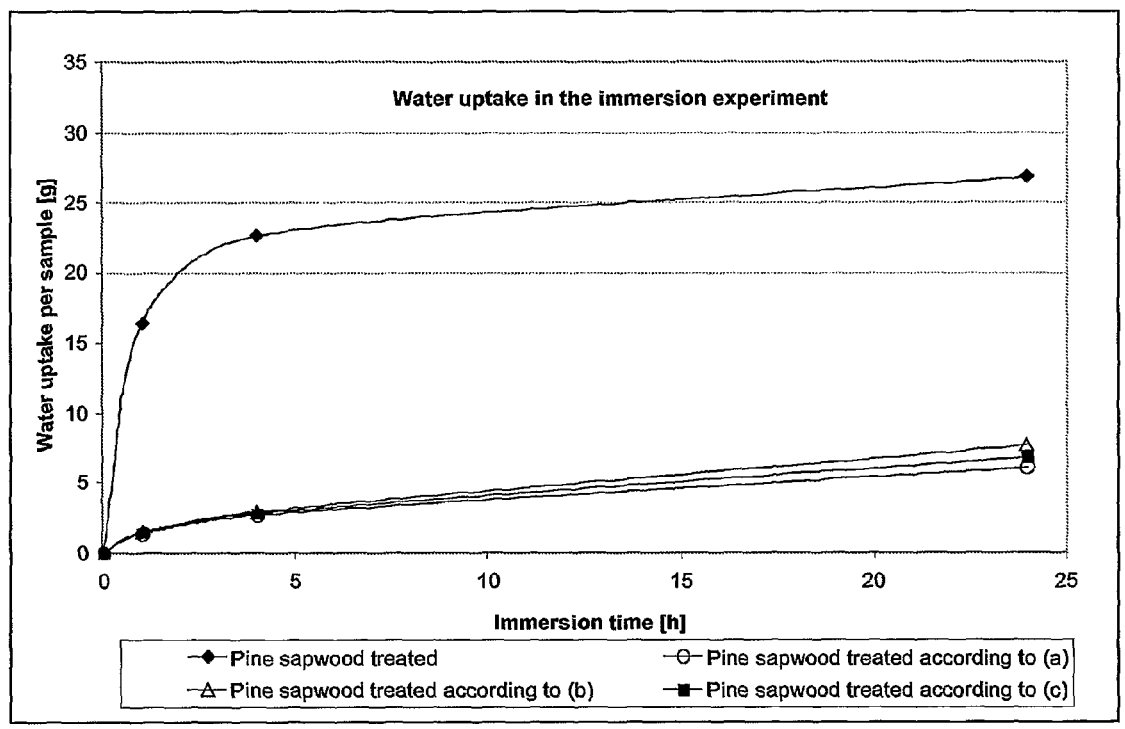
Fig. 2 for example 2: Reduction of water uptake of wood in the immersion experiment (imparting of water repellency)

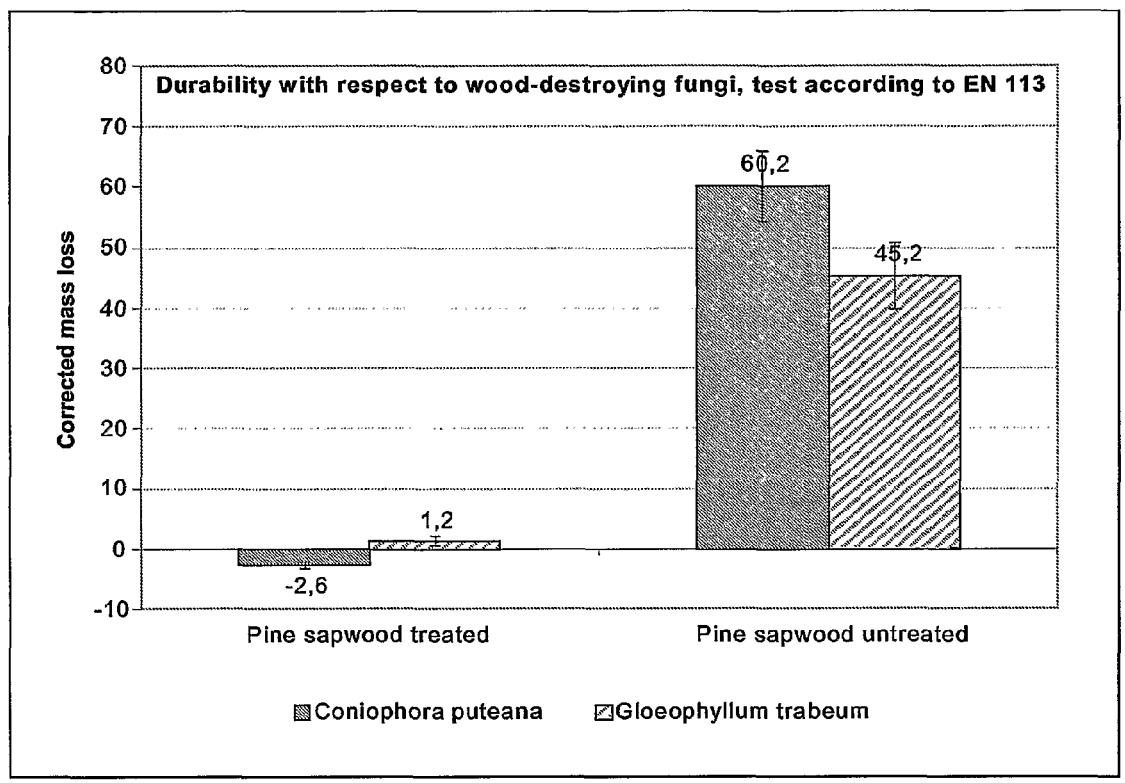
Fig. 3 for example 3: Durability with respect to wood-destroying brown rot fungi

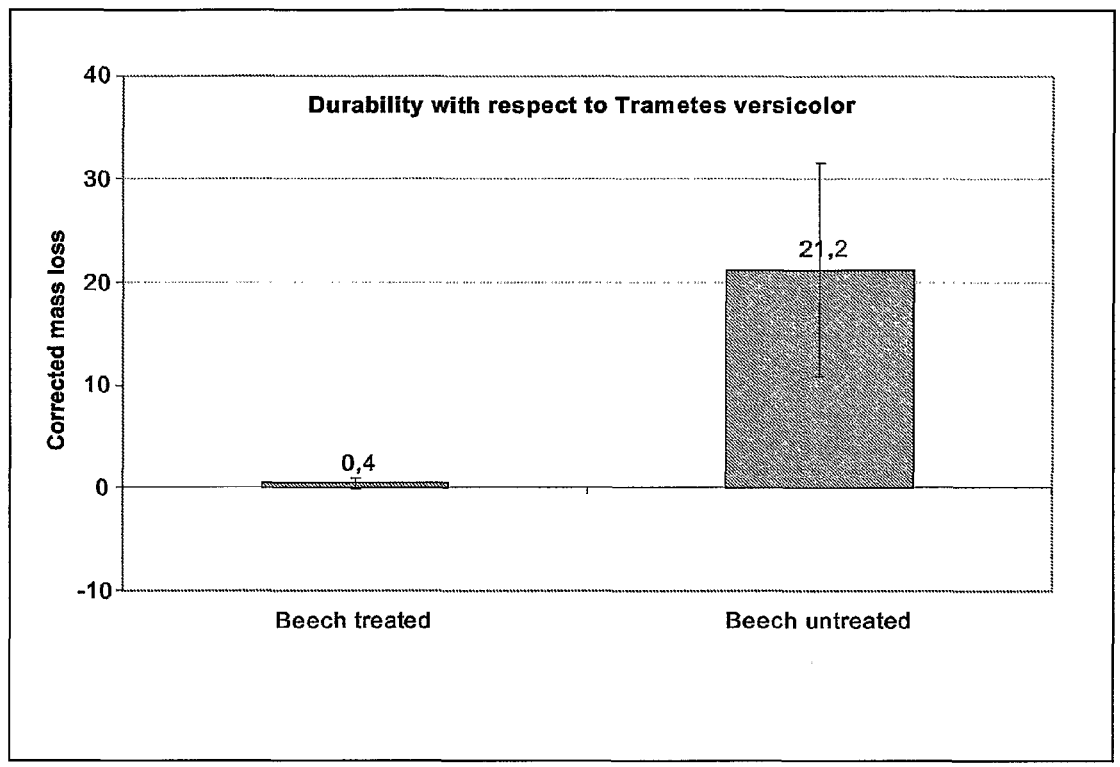
Fig. 4 for example 4: Durability with respect to the wood-destroying white rot fungi *Trametes versicolor*

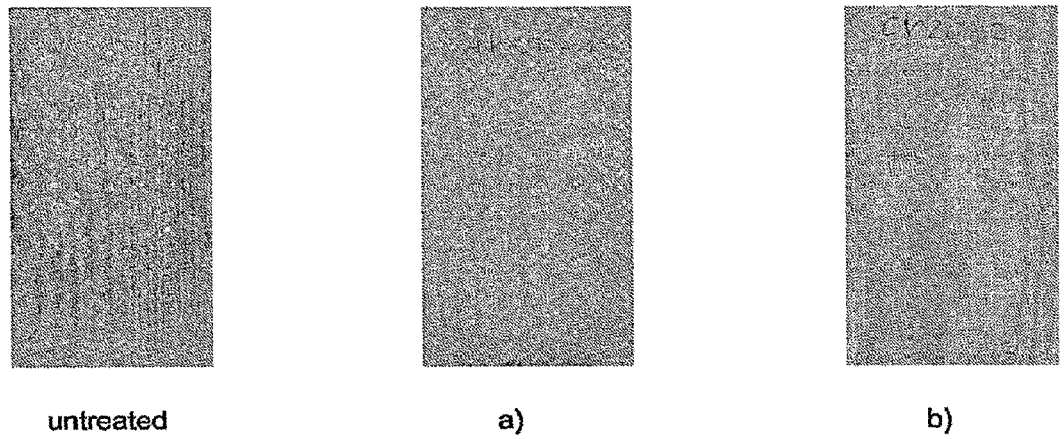
Fig. 5 for example 5: View of the unweathered, reverse sides of samples (pine sapwood) after weathering for one year according to EN 927
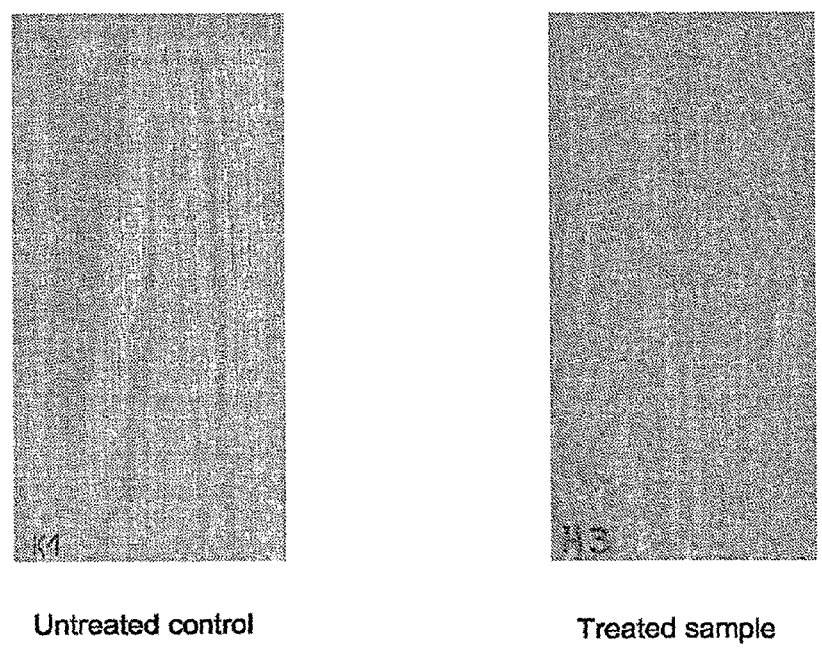
Fig. 6 for example 9: Samples of pine sapwood after weathering for two weeks in the QUV weathering apparatus

AGENT FOR PROVIDING SUBSTRATES BASED ON CELLULOSE AND/OR STARCH WITH WATER REPELLENT AND SIMULTANEOUSLY ANTIFUNGAL, ANTIBACTERIAL INSECT-REPELLENT AND ANTIALGAL PROPERTIES

The invention relates to agents containing silicon compounds and intended for protective treatment of substrates based on cellulose and/or starch, the use thereof and a special treatment process using such agents.

Following the very extensive use of durable tropical wood species, for example in the construction element sector in the 70s and 80s, measures for restricting the use of tropical timber, some of which were very restrictive, were taken in several European countries, for example through directives for tenders in the communal sector. However, the consequent reduced consumption of tropical timbers did not automatically mean an improvement in the environmental situation. Rather, it was to be observed that there was a greater tendency to clearance by fire owing to the consequently reduced value of the forests. It was also evident that, for sustained development in the producer countries, the people living there would have to be offered economic prospects. Against this background, certification systems which established, in particular environmental and social standards and assessed forests according to these were developed. Certification according to FSC and according to PEFC have become established and are the most well known systems. In the year 2003, the Federal German Ministry of the Environment recommended FSC-certified wood, but the two systems are considered to be comparable. As a result of the certification, the situation is now somewhat more relaxed, but restrictions of the use of tropical timbers are still in force.

Under the present general conditions, it is expedient to include not only indigenous timbers but also tropical timbers in the chemical modification of wood, substantially from the points of view of "certification of the forests" and "impregnatability of the wood".

Thus, inter alia, the fast-growing rubber wood which is typically cultivated in plantations or obtained as waste and which has little natural durability is a suitable substrate for chemical modification owing to the good treatability, availability and processability and the advantageous price.

By improving the properties of indigenous timbers, it was possible to replace tropical timbers having high durability. Environmental aspects and the associated public discussion with corresponding legislative trends are important arguments also for chemical modification of indigenous wood species.

Inter alia, wood as a material is distinguished by good strength properties and good processability and is therefore used, for example, in the construction sector and in furniture construction and interior trim. However, certain properties typical of wood restrict the use of wood. Thus, the dimensional changes on change of humidity due to swelling and shrinkage has an adverse effect on the dimensional stability of structural parts and the adhesion of coats. Wood components may be chemically changed and eroded also as a result of UV radiation. The poor durability, in particular in the presence of fungi and insects, necessitates in some cases the use of biocides or of resistant wood species, for example certain tropical timbers.

The chemical modification of wood may be one way to improve the competitive situation of timbers having little durability. Efforts are made, inter alia, to increase the durability, to change the sorption behavior and to increase the dimensional stability of wood, with the result that the maintenance intervals and the life of components made of wood are to be increased in the end. Thus, efforts are also being made to improve the durability with respect to wood-destroying organisms without the use of biocides which are harmful to the environment and health, in particular in view of the legal situation in the area of the chemical protection of wood.

In the chemical treatment of wood, it is possible in principle to distinguish between surface protection and full protection. In the case of surface protection, the regions close to the surface are treated, i.e. a few millimeters of depth of penetration, or only a layer is produced on the surface. As a result, for example, water repellency of the wood, an increase in the hardness or improved UV stability can be achieved. In the case of full protection, the entire wood sample is penetrated by the impregnating composition. Development work on the chemical modification of wood furthermore indicates that the effect is also determined by the penetration of the chemical into the cell wall and the fixing there, for example by blocking of the hydroxyl groups of the cellulose. Thus, inter alia, a large number of silicon compounds which have a very wide range of properties and are used as water repellents, for example, in the construction, paper and textile industry has been described.

WO 01/97985 discloses a process for the treatment of wood, alkyl- and arylalkoxysilanes, corresponding chlorosilanes and also organic titanates, borates and phosphorus compounds being used in the presence of a catalyst and optionally in solution in an organic solvent.

EP 0 747 184 A2 relates to protection and consolidation compositions for renewable raw materials, such as starch products, cellulose products and/or the degradation products thereof, the composition being based on a modified metal oxide organosol and being capable of containing, if required, further additives, such as water, water-soluble organic solvents, hydrolysis products of organically substituted trialkoxysilanes, active substances against wood-damaging organisms or inorganic or organic biocides. The treatment is effected by immersion, brushing or spraying of the raw materials with the treatment composition, gelling of the sol and subsequent drying of the preparations. Thus, the composition is used for the long-term protection of said raw materials against harmful organisms or against corrosive media or fire, for the sealing or masking of wood surfaces, for long-lasting dimensional stabilization and for strengthening of the surfaces of wood or moldings and for replacement of chromium compounds contained in wood preservatives for fixing.

DE 39 00 303 A1 discloses a process for the impregnation of wood using alkyltrialkoxysilanes having an alkyl radical of 3 to 18 carbon atoms for reducing the water absorption. Thus, for example, pine wood is immersed in the silane liquid and then dried at from 40 to 90° C.

DE-OS 29 03 376 teaches a process for the production of wood impregnated with plastic in a vacuum pressure process, cf. also DE 198 33 479 A1.

DE 101 22 627 A1 describes a process for water-repellent wood treatment with, inter alia, amino-functional polydimethylsiloxanes or a mixture of octyltrimethoxysilanes, tetraethoxysilane and methylsilicone resin with crosslinking with butyl titanate.

EP 0 385 108 A2 discloses the use of organosilicon compounds, inter alia cationic trialkoxysilanes, for the water-repellent and antimicrobial impregnation of inorganic oxidic materials, such as stone, masonry and concrete.

EP 0 846 668 B1 describes an aqueous formulation which contains organic polymers, such as functionalized polybutene, and an organoalkoxysilane, silanes having amino and ammonium functionalities being excepted. Such formulations are likewise used for providing cellulose-containing surfaces with water-repellent properties.

EP 0 882 555 A2 relates to a process for the production of wood provided with antibacterial/antifungal inorganic substances, the wood being treated with a solution which contains an alkoxysilane and an antibacterial/antifungal organoalkoxysilicon compound. In particular, reference is made to the use of organoalkoxysilicon compounds which contain quaternary N,N-dimethylammonium halide functionalities.

EP 0 716 127 B1 and EP 0 716 128 B1 describe water-based aminoalkyl-/alkyl-/hydroxyl- or alkoxy-siloxane-containing compositions which are used, inter alia, for imparting water repellency to textiles, leather, cellulose products and starch products. Such aminoalkylorganohydroxysiloxanes which are soluble in water or water/alcohol mixtures are also referred to as hydrosil systems. Regarding fluoroalkyl-functional hydrosil systems, reference may additionally be made to EP 0 846 716 B1, EP 0 846 717 B1 and EP 1 101 782 A2.

It was therefore the object of the present invention to provide a further possibility for the treatment of cellulose- and/or starch-containing substrates, it being particularly desired to protect less durable commercial timbers in a manner as environmentally compatible as possible from the influence of water, fungi, bacteria, insects and/or algae.

The object was achieved, according to the invention, according to the statements of the patent claims.

BRIEF DESCRIPTION OF DRAWINGS

FIG. 1. Graphic representation of sorption behavior of samples in example 1 on conditioning.

FIG. 2. Graphic representation of reduction of water uptake of wood in the immersion experiment (imparting of water repellency) in example 2.

FIG. 3. Graphic representation of durability with respect to wood-destroying brown rot fungi of treated samples in example 3.

FIG. 4. Graphic representation of durability with respect to the wood-destroying white rot fungi Trametes versicolor of treated samples in example 4.

FIG. 5. Back views of the untreated and treated samples (pine sapwood) after weathering for one year according to EN 927 in example 5. Samples treated with a water-repellent alkylalkoxysilane (a) and with aqueous DYNASYLAN HS 2909 with dilution 33% (w/w) (b).

FIG. 6. Untreated and treated samples of pine sapwood after weathering for two weeks in a QUV weathering apparatus in example 9.

Thus, it was surprisingly found that, for example, but not exclusively, readily impregnatable timbers, such as beech or pine, can be provided with hydrophobic and simultaneously antifungal, antibacterial, insect-repellent and/or antialgal properties if the cellulose and/or starch substrate is treated with a dilute aqueous composition which contains at least one organosiloxane or a mixture of organosiloxanes of the general formula I

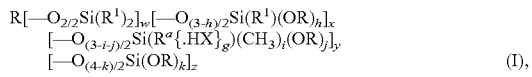

(I), in which groups R are identical or different and R is substantially H, optionally methyl, ethyl or isopropyl or n-propyl and optionally a silyl radical having the silyl units according to formula I, groups $R^1$ are identical or different and $R^1$ is a linear, branched or cyclic, optionally substituted alkyl group having 1 to 18 carbon atoms, preferably—but not exclusively—methyl, n-propyl, isobutyl, n-octyl, partly fluorinated or perfluorinated alkyl groups, in particular tridecafluoro-1,1,2,2-tetrahydrooctyl, heptadecafluoro-1,1,2,2-tetrahydrodecyl, isooctyl, hexadecyl—to name but a few, $R^a$ is an aminoalkyl group of the general formula (Ia) $H_2N(CH_2)_d[(NH)_e(CH_2)_f]_\beta$—, in which $0 \leq d \leq 6$, $0 \leq f \leq 6$, e equals 0, if d equals 0, then β equals 1, e equals 1, if d>0, then β equals 1 or 2, preferably 3-aminopropyl, N-(2-aminoethyl)-3-aminopropyl, N-[N'-(2-aminoethyl)-2-amino-ethyl]-3-aminopropyl, N,N-[di-(2-aminoethyl)]-3-aminopropyl, N-(n-butyl)-3-aminopropyl, groups X are identical or different and X is an organic or inorganic acid radical from the series consisting of chloride, formate, acetate and phosphate, where g equals 0 or 1 or 2 or 3, preferably formate or acetate, h, i and j, independently of one another, are 0 or 1 and k is 0, 1, 2 or 3 and x, y, z and w are identical or different and x is a number from 0 to 50, preferably from 3 to 45, particularly preferably from 5 to 40, in particular from 10 to 30, y is a number from 1 to 50, preferably from 3 to 45, particularly preferably from 5 to 40, in particular from 10 to 30, z is a number from 0 to 10, preferably from 0.001 to 5, particularly preferably from 0.01 to 3, in particular from 0.1 to 2, and w is a number from 0 to 30, preferably from 0.001 to 10, particularly preferably from 0.1 to 5, in particular from 0.5 to 3, with (w+x)≧1, preferably (w+x+z)>1, and this composition is allowed to act. Suitable methods for this purpose are, for example, painting, spraying, immersion, flooding, steeping, pressure process, vacuum impregnation, vacuum pressure impregnation, borehole impregnation and the Boucherie process. This is usually followed by a drying process. Vacuum pressure impregnation in combination with a specific drying process has proven particularly advantageous.

In addition, the composition used here, also referred to below as agent, may advantageously contain further components, for example free acids, alcohols, selected alkylsilanes and cationic monomeric aminosilanes, the effect of the components may be regarded in each case as a combination of the components of the agent. Moreover, further additives, such as flameproofing agents, UV stabilizers, insecticides and crop protection agents, aromas and colored pigments, may be added.

Thus, preparations which were subjected to a treatment according to the invention are found to have not only excellent, long-lasting hydrophobic properties and at the same time an outstanding resistance to basidiomycetes, in particular of the group consisting of the brown rot and white rot fungi, but also comparable sorption properties and swelling and shrinkage.

The particular advantageous suppression of wood degradation by wood-destroying fungi, in particular white rot and brown rot should be emphasized in particular. Furthermore, the hydrophobic effect results in a substantial reduction of attack by wood-discoloring fungi on persistent weathering, in particular blue fungi and surface fungi, such as, for example, molds. Furthermore, the influence of bacteria, insects and algae can be advantageously reduced by the treatment according to the invention.

In addition, present preparations have good resistance to UV light and, after coating, also good adhesive power of the coat to the treated substrate. Substrates treated according to the invention are also distinguished by improved hardness and fire resistance.

The present invention therefore relates to an agent for providing substrates based on cellulose and/or starch as water-repellent and simultaneously antifungal, antibacterial, insect-repellent and antialgal properties, which contains water and, as active substance, at least one linear, cyclic, branched or crosslinked co-oligomer or mixtures of co-oligomers from the series consisting of the alkyl-/aminoalkyl-/alkoxy- or hydroxy-siloxanes, such co-oligomers substantially satisfying the general formula I

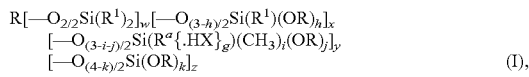

$$R[-O_{2/2}Si(R^1)_2]_w[-O_{(3-h)/2}Si(R^1)(OR)_h]_x$$
$$[-O_{(3-i-j)/2}Si(R^a\{.HX\}_g)(CH_3)_i(OR)_j]_y$$
$$[-O_{(4-k)/2}Si(OR)_k]_z \quad (I),$$

in which groups R are identical or different and R is substantially H, optionally methyl, ethyl or isopropyl or n-propyl and optionally a silyl radical having the silyl units according to formula I, groups $R^1$ are identical or different and $R^1$ is a linear, branched or cyclic, optionally substituted alkyl group having 1 to 18 carbon atoms, $R^a$ is an aminoalkyl group of the general formula (Ia) $H_2N(CH_2)_d[(NH)_e(CH_2)_f]_\beta-$, in which $0 \leq d \leq 6$, $0 \leq f \leq 6$, e equals 0, if d equals 0, then β equals 1, e equals 1, if d>0, then β equals 1 or 2, groups X are identical or different and X is an organic or inorganic acid radical from the series consisting of chloride, formate, acetate and phosphate, where g equals 0 or 1 or 2 or 3, h, i and j, independently of one another, are 0 or 1 and k is 0, 1, 2 or 3
and x, y, z and w are identical or different and x is a number from 0 to 50, y is a number from 1 to 50, z is a number from 0 to 10 and w is a number from 0 to 30, with $(w+x) \geq 1$.

Agents according to the invention are as a rule obtainable by hydrolysis and cocondensation of corresponding monomeric alkoxy- or chlorosilanes by addition of an amount of water required for obtaining the desired degree of oligomerization. The procedure may be carried out in the presence of a hydrolysis or condensation catalyst. Furthermore, the hydrolysis and cocondensation can be carried out in the presence of a diluent or solvent, preferably methanol, ethanol and/or isopropanol. As a rule, alcohol or solvent is removed at least proportionally from the system after or during the reaction, and the system is diluted to the desired extent with water. In addition, further components may be added to the agent present, for example additional acid, alcohol, monomeric organosilanes or monomeric cationic aminosilanes. The preparation of corresponding systems and starting materials suitable for this purpose are, however, also described in EP 0 716 127, EP 0 716 128, EP 0 846 717, EP 0 846 716 and EP 1 101 787. The total content of the patents mentioned herein is hereby incorporated in its entirety in the disclosure of the present Application.

The units shown in square brackets and indexed with w, x, y and z in formula I can be present for R as silanol groups in up to 100% of the possibilities. However, it may also be less, for example up to 90%, in which case optionally alkoxy groups are also present, for example in up to 2% of the possibilities, and R may also be a silyl radical comprising at least one unit of the present oligomers according to formula I, so that, on the basis of chemical understanding, the structure of the siloxane can then be realized in linear, branched or cyclic form here. Linear or cyclic silane oligomers according to formula I are preferably present, i.e. as a rule comparatively short-chain organosiloxanes which are substantially composed of M- and D-structures are present here. However, branched structures or three-dimensional structures, i.e. organosiloxanes according to formula I having T- or Q-structures, may also occur now and again, but then in a substantially minor amount.

Agents according to the invention preferably have a content of active substance according to formula I of from 0.5 to 95% by mass, particularly preferably from 2 to 40% by mass, very particularly preferably from 5 to 30% by mass, in particular from 5 to 20% by mass, based on the composition.

Thus, compounds according to formula I, for example DYNASYLAN® HS 2909, F 8800 or F 8815, can advantageously be mixed in the desired ratio with water. The abovementioned products or agents also can first be mixed and then optionally diluted with water and/or alcohol. For example, a triaminoalkyl/tridecafluoro-1,1,2,2-tetrahydrooctyl/hydroxy- or alkoxy-siloxane mixture substantially neutralized with acetic acid or formic acid, or 3-aminopropyl/isobutyl/hydroxy- or alkoxy-siloxane mixture substantially neutralized with acetic acid, can be mixed with water in the volume ratio of about 1:0.5 to 0.5:5, preferably about 1:1 to 0.5:2, in particular about 1:2.

An agent according to the invention which contains from 5 to 99.5% by mass, particularly preferably from 50 to 98% by mass, of water, very particularly preferably from 60 to 95% by mass, in particular from 80 to 95% by mass, based on the composition, is preferred, the respective components of the agent or of a composition being 100% by mass in total.

An agent according to the invention may also contain <10% by mass, preferably from 0 to 7% by mass, particularly preferably from 0.001 to 5% by mass, based on the composition, of free acid, i.e. acid moieties which are present as ammonium salt in the context of the formula I according to $\{.HX\}_g$ are to be excluded here with reference to the so-called free acid moieties.

Furthermore, an agent according to the invention may have a content of alcohol, in particular methanol, ethanol, n-propanol, isopropanol, 2-methoxyethanol or a mixture thereof, of less than 95% by mass, preferably from 0.001 to 10% by mass, particularly preferably from 0.01 to 5% by mass, in particular from 0.1 to 3% by mass, based on the composition.

In addition, an agent according to the invention may advantageously contain from 0 to 6% by mass, preferably from 0.1 to 5% by mass, particularly preferably from 1 to 4% by mass, of at least one alkylsilane or corresponding hydrolysis products or partial hydrolysis products from the series consisting of tetraethoxysilane, methyltriethoxysilane, n-propyltriethoxysilane, isobutyltriethoxysilane, n-octyltri-ethoxysilane or isooctyltriethoxysilane, perfluoropropyltriethoxysilane, tridecafluoro-1,1,2,2-tetrahydrooctyltriethoxysilane or heptadecafluoro-1,1,2,2-tetrahydrodecyltri-ethoxysilane, the data being based in each case on the composition.

Furthermore, agents according to the invention may advantageously contain siloxanes which have alkyl groups and fluoroalkyl groups as groups $R^1$ according to formula I, e.g. alkyl and fluoroalkyl groups $R^1$ may be present here alongside one another in an oligomer. As such, however, oligomers can also be present alongside one another, in the oligomer molecule of the mixture either exclusively unsubstituted alkyl groups or only fluoroalkyl groups $R^1$ being present in a molecule. As already described above, such mixtures can be prepared, for example, by mixing compounds according to formula I, in particular DYNASYLAN® HS 2909 with F 8800 or 8815. However, it is also possible to use corresponding alkylsilanes and fluoroalkylsilanes as a mixture in the preparation of the hydrosils.

Thus, the proportion of fluoroalkyl groups, based on all alkyl groups $R^1$ according to formula I, can advantageously be from 0.001 to 90 mol %, preferably from 0.005 to 50 mol %, particularly preferably from 0.01 to 10 mol %, very particularly preferably from 0.05 to 5 mol %, in particular from 0.1 to 1 mol %.

It may also be advantageous for the agent according to the invention to contain at least one cationic aminoalkylsilane of the general formula II

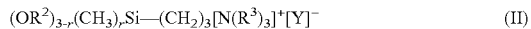
$$(OR^2)_{3-r}(CH_3)_r Si\text{—}(CH_2)_3[N(R^3)_3]^+[Y]^- \quad \text{(II)}$$

in which groups $R^2$ are identical or different and $R^2$ is H, methyl, ethyl or isopropyl or n-propyl, r equals 0 or 1, groups $R^3$ are identical or different and $R^3$ is H or a linear, branched or cyclic $C_1$- to $C_{18}$-alkyl group and $[Y]^-$ is chloride, formate, acetate or a phosphate radical.

For example, the agent may contain, inter alia, a proportion of at least one compound from the series consisting of N-[3-(trimethoxysilyl)propyl]-N,N,N-trimethylammonium chloride, N-[3-(trimethoxysilyl)propyl]-N,N,N-triethylammonium chloride, N-[3-(tri-ethoxysilyl)propyl]-N,N,N-trimethylammonium chloride, N-[3-(triethoxysilyl)propyl]-N,N,N-triethylammonium chloride, N-[3-(trimethoxysilyl)propyl]-N-octadecyl-N,N-di-methylammonium chloride, N-[3-(triethoxysilyl)propyl]-N-octadecyl-N,N-dimethylammonium chloride, N-[3-(triethoxysilyl)propyl]-N-benzyl-N,N-dimethylammonium chloride, N-[3-(triethoxysilyl)propyl]-N-dodecyl-N,N-dimethylammonium chloride, N-[3-(trimethoxysilyl)propyl]-N-dodecyl-N,N-dimethylammonium chloride, N-[3-(tri-methoxysilyl)propyl]-N,N-didodecyl-N-methylammonium chloride, N-[3-(triethoxysilyl)-propyl]-N-tetradecyl-N,N-dimethylammonium chloride, N-[3-(trimethoxysilyl)propyl]-N-tetradecyl-N,N-dimethylammonium chloride, N-[3-(triethoxysilyl)propyl]-N-hexadecyl-N,N-dimethylammonium chloride, N-[3-(trimethoxysilyl)propyl]-N-hexadecyl-N,N-di-methylammonium chloride and N-[3-(tri-methoxysilyl)propyl]-N,N,N-trimethyl-ammonium hydroacetate. The agent can also advantageously contain chloride-free compounds, i.e. in particular corresponding formates or acetates of the above-mentioned compounds.

Thus, according to the invention, a preferred agent is one which contains <20% by mass of a compound of the general formula II. From 0.001 to 10% by mass are particularly preferred, very particularly preferably from 0.01 to 7% by mass, in particular from 0.1 to 5% by mass, based on the composition.

Agents according to the invention are as a rule colorless to brown, clear liquids having a viscosity of from about 0.5 to $10^3$ mPa s.

The present invention likewise relates to a novel process for providing substrates based on cellulose and/or starch with water-repellent and simultaneously antifungal, antibacterial, insect-repellent and antialgal properties, the substrate being treated with an agent according to the invention and then being dried.

The substrate used may be in particular wood, for example impregnatable timbers, such as beech, spruce, pine or rubber wood, it being possible to store the substrate, for example, in the open air, as is customary with wood, and as a rule to establish a wood moisture content of from 12 to 18%. The wood moisture content is usually determined according to DIN 52 183. As is customary in wood treatment, the substrate can be treated in the sap-fresh to thoroughly dry state, preferably between the sap-fresh state and a wood moisture content of 6%, in particular at a wood moisture content of from 10 to 25%.

In the process according to the invention, the substrate can be coated or impregnated by all methods customary in wood treatment and known from the technical literature for introducing aqueous solutions of the agent according to the invention, such as, for example, but not exclusively, by painting, spraying, immersion, flooding, steeping, pressure process, vacuum impregnation, vacuum pressure impregnation and borehole impregnation or by the Boucherie process, cf. also "Holzlexikon von A-Z" [Wood lexicon from A to Z] (Volumes I and II), Ulf Lohmann, DRW-Verlag, Leinfelden-Echterdingen, 2003, cf. inter alia "Einbringverfahren" [Methods of impregnation], Volume I, pages 289 to 292.

In the process according to the invention, a pressure process or a surface treatment process, such as painting, spraying, immersion or flooding, is preferably carried out. Particularly preferably, a vacuum pressure impregnation is carried out in the process according to the invention.

For this purpose, for example, but not exclusively, it is possible to adopt a procedure in which the substrate to be impregnated is first exposed to a pressure of from 10 to 500 mbar, preferably from 50 to 200 mbar, in particular about 100 mbar abs., in a pressure-resistant impregnation reactor, for from 5 minutes to 8 hours, preferably from 15 minutes to 2 hours, in particular from about half an hour to one hour, this pressure is maintained and the substrate is immersed in the impregnating agent or covered with the impregnating agent, for example by flooding, and the pressure is increased to from 1.5 to 20 bar for from 0.5 to 4 hours, preferably to from 5 to 15 bar for from 1 to 3 hours, in particular to from 10 to 12 bar about for from 2 to 3 hours. Thereafter, the pressure can be reduced to ambient pressure. The substrate is removed from the impregnating solution, optionally a subsequent vacuum is allowed to act and said substrate is allowed to drip and the substrate impregnated by the vacuum pressure process in this manner is fed to the drying stage.

In the process according to the invention, a specific drying process is advantageously carried out on the impregnated substrate after the impregnation step. Thus, in the process according to the invention, the impregnation step should be followed by specific air drying and/or a specific industrial drying process, for example, but not exclusively, microwave drying, IR drying, fresh air/exhaust air drying, hot air drying, vacuum drying, freeze drying or a combination of the methods, as described, for example, in "Holzlexikon von A-Z" [Wood lexicon from A to Z] (Volumes I and II), Ulf Lohmann, DRW-Verlag, Leinfelden-Echterdingen, 2003, cf. inter alia "Holztrocknung" [Wood drying], Volume I, page 605.

The drying step is preferably carried out at a temperature between ambient temperature, i.e. outdoor temperature or room temperature, and 250° C., from 50 to 250° C. being particularly preferred for the drying of wood-base materials, such as fibers, chips and veneers, and up to 140° C. being particularly preferred for solid wood products. The drying time is as a rule dependent on the wood species and the dimensions of the material, the advantageous drying time also being revealed in the examples.

The inventive drying step of the present process is important for the chemical or physical fixing of the active substances of the agent used here to the cellulose or starch substrates. By varying the parameters, it is possible advantageously to adapt the desired properties of the compounds according to the invention by condensation or chemical bonding to the substrate surface.

In the process according to the invention, drying therefore also means fixing of the impregnation active substances to the substrate in a manner which protects the product as far as possible. Thus, the substrate impregnated according to the invention can be dried as described above but, in the process according to the invention, the combination of the impregnation step according to the invention with a particularly product-protecting drying step which moreover may include an additional thermal treatment for further improved fixing of the active substances of the impregnating agent is particularly preferred.

Thus, in particular surface-impregnated, partly impregnated or completely impregnated wood can first be dried at from ambient temperature or room temperature to 250° C., preferably up to 180° C., but particularly preferably also at from 20 to 120° C., very particularly preferably at from 40 to about 60° C.

Advantageously, the atmospheric humidity can also be controlled, for example in a conditioning chamber, it being possible to reduce the atmospheric humidity in a controlled manner over one day to eight weeks, preferably one to four weeks, and optionally to regulate the temperature until a wood moisture content of <30%, preferably from 6 to 20%, particularly preferably from 12 to 18%, in particular about 15%, has been reached.

It is also possible to ensure good turbulence of the air in the drying chamber or conditioning chamber during the drying.

Thus, for example, but not exclusively, the drying program may start at a temperature between 10 and 130° C., in particular at from 30 to 60° C., and at from 80 to 100% relative humidity, the moisture first suitably being reduced, after which the temperature can be increased.

However, it is also possible to keep the relative humidity initially substantially constant at a high level and to increase the temperature in order subsequently to reduce the relative humidity to a medium value at higher temperature and optionally also to leave some time before reducing the temperature to ambient temperature.

However, the impregnated substrate can also be allowed to dry under outdoor conditions (air drying) and then—if required for the subsequent application—be thermally aftertreated, for example at a temperature in the range between 40 and 250° C. in a drying chamber or conditioning chamber. The drying may take a few hours or days to several weeks.

Substrates which, for example, but not exclusively, are to have a particular leaching resistance of the siloxane active substances or to have additional hardness can be finally dried or thermally treated preferably at from 80 to 160° C., in particular at about 100 to 140° C.

In the process according to the invention, calculated drying can also advantageously be effected by a procedure in which the impregnated substrate is dried, optionally in the open air (air drying), preferably for from 2 days to 6 weeks, in particular from about 4 days to 4 weeks, until a wood moisture content of from 12 to 18% is established, and then
(i) treated for from 2 hours to 4 weeks, preferably from about 6 hours to 3 weeks, at from 50 to 120° C., preferably from about 60 to 70° C., i.e. as fresh air drying or exhaust air drying, or
(ii) dried for from 2 hours to 4 weeks, preferably from 4 hours to 10 days, at from about 50 to 60° C. and optionally aftertreated for from a further 2 to 48 hours at about 120° C. or
(iii) drying in a conditioning chamber or drying with superheated steam, i.e. at >90% moisture saturation of the heated air, is carried out for from 2 hours to 2 weeks, preferably from 6 to 180 hours, at from about 50 to 130° C., preferably from 105 to 120° C.

In general, the process according to the invention for the treatment of substrates based on cellulose or starch is carried out as follows:

An aqueous agent according to the invention for carrying out the substrate impregnation is used in a suitable manner. For this purpose, the substrate can be preconditioned, for example, by conventional industrial drying or conventional storage, i.e. storage in the open air. The substrate to be treated is then brought into contact with the impregnating agent, for example by immersion or flooding in a reactor or container suitable for this purpose, the substrate being completely covered by the agent in a suitable manner. Before or during the impregnation, the pressure can be set or varied. A vacuum pressure impregnation is preferably carried out in a manner known per se. Thus, the substrate can be impregnated under reduced pressure, at atmospheric pressure or at superatmospheric pressure. It is also possible to vary the pressure once or several times while carrying out the impregnation. The preparation is discharged in a suitable manner after the impregnation, and the substrate thus impregnated is then fed to a targeted drying process, for example in a conditionable drying chamber. After targeted drying or thermal postconditioning of the impregnated substrate, a substrate treated according to the invention and having all its advantages listed above is obtained.

Thus, the present invention also relates to the use of an agent according to the invention for the treatment of wood or wood products.

Thus, an agent according to the invention is particularly advantageously used for providing wood or wood products with water-repellent and simultaneously antifungal, antibacterial, insect-repellent and/or antialgal properties.

In particular, the protection of wood and wood products from the effects which are due to wood-degrading or wood-discoloring fungi (mold, blue fungi), in particular brown rot fungus and white rot fungus, can thus be ensured.

According to the invention, an agent which contains silane co-oligomers according to formula I in an amount of from 0.5 to 95% by mass, based on the composition of the agent, is advantageously used, and the preparation of the silane oligomer mixture is advantageously based on a molar ratio of aminoalkoxysilane to alkylalkoxysilane of from 4:1 to 1:4, suitably from 2:1 to 1:1. In particular, 3-aminopropyltrimethoxy-silane (AMMO), 3-aminopropyltriethoxysilane (AMEO) and DYNASYLAN® TRIAMO may be mentioned as examples of aminoalkoxysilanes, and isobutyltrimethoxysilane (DYNASYLAN® IBTMO), isobutyltriethoxysilane (DYNASYLAN® IBTEO), 2-amino-ethyl-3-aminopropyltrimethoxysilane (DYNASYLAN® DAMO), methyltrimethoxysilane (DYNASYLAN® MTMS) and methyltriethoxysilane (DYNASYLAN® MTES) may be mentioned as examples of alkylalkoxysilanes.

According to the invention, it is furthermore possible to use an agent which contains silane co-oligomers according to formula I in an amount of from 0.5 to 95% by mass, based on the composition of the agent, and from 0.001 to 55 mol % of the alkylalkoxysilane used are replaced by a corresponding molar amount of at least one further alkylalkoxysilane and/or tetraalkoxysilane, in particular tetraethoxysilane (DYNASIL® A) in the preparation of the silane oligomer mixture.

According to the invention, it is furthermore possible to use an agent which contains silane co-oligomers according to formula I in an amount of from 0.5 to 95% by mass, based on the composition of the agent, and to base the preparation of the silane oligomer mixture on a molar ratio of aminoalkoxysilane to fluoroalkylalkoxysilane of from 3:1 to 1:3.33, preferably from 2:1 to 1:3. Thus, in particular, but not exclusively, DYNASYLAN® F 8261 can be used as the fluoroalkylalkoxysilane.

According to the invention, it is also possible to use an agent which contains silane co-oligomers according to formula I in an amount of from 0.5 to 95% by mass, based on the composition of the agent, and to replace from 0.001 to 99.999 mol % of the fluoroalkylalkoxysilane used by a corresponding molar amount of at least one alkylalkoxysilane and/or tetraalkoxysilane in the preparation of the silane oligomer mixture. Thus, for example, the following combinations may be preferred: DYNASYLAN® AMEO with DYNASYLAN® F 8261/DYNASIL® A; DYNASYLAN® AMEO with DYNASYLAN® F 8261/DYNASYLAN® PTEO; DYNASYLAN® AMEO with DYNASYLAN® F 8261/DYNASYLAN® MTES; DYNASYLAN® AMEO with DYNASYLAN® F 8261/DYNASYLAN® IBTMO; DYNASYLAN® AMEO with DYNASYLAN® F 8261/ DYNASYLAN® OCTEO; DYNASYLAN® AMEO with DYNASYLAN® F 8261/DYNASYLAN® PTEO/DYNASIL® A; DYNASYLAN® AMEO with DYNASYLAN® F 8261/DYNASYLAN® IBTMO/DYNASIL® A; DYNASYLAN® DAMO with DYNASYLAN® F 8261/DYNASYLAN® DAMO with DYNASYLAN® F 8261/DYNASYLAN® PTEO; DYNASYLAN® DAMO with DYNASYLAN® F 8261/DYNASYLAN® MTES; DYNASYLAN® DAMO with DYNASYLAN® F 8261/DYNASYLAN® IBTMO; DYNASYLAN® DAMO with DYNASYLAN® F 8261/DYNASYLAN® OCTEO; DYNASYLAN® DAMO with DYNASYLAN® F 8261/DYNASYLAN® PTEO/DYNASIL® A; DYNASYLAN® DAMO with DYNASYLAN® F 8261/DYNASYLAN® IBTMO/DYNASIL® A; DYNASYLAN® TRIAMO with DYNASYLAN® F 8261/DYNASIL® A; DYNASYLAN® TRIAMO with DYNASYLAN® F 8261/DYNASYLAN® PTEO; DYNASYLAN® TRIAMO with DYNASYLAN® F 8261/DYNASYLAN® MTES; DYNASYLAN® TRIAMO with DYNASYLAN® F 8261/DYNASYLAN® IBTMO; DYNASYLAN® TRIAMO with DYNASYLAN® F 8261/ DYNASYLAN® OCTEO; DYNASYLAN® TRIAMO with DYNASYLAN® F 8261/DYNASYLAN® PTEO/DYNASIL® A; DYNASYLAN® TRIAMO with DYNASYLAN® F 8261/DYNASYLAN® IBTMO/DYNASIL® A, to mention but a few examples.

The ratios of said functional organosilanes or silicic esters may vary within a very wide range, where the proportion of the amino-functional component or the cationized or neutralized amino-functional component is preferably from 0.1 to 40 mol %, particularly preferably from about 10 to 30 mol %.

According to the invention, it is also possible to use an agent which contains silane co-oligomers according to formula I in an amount of from 0.5 to 95% by mass, based on the composition of the agent, and the silane co-oligomer mixture is prepared by mixing an aminoalkyl-/alkyl-/hydroxy- or alkoxy-functional siloxane mixture A with an aminoalkyl-/fluoroalkyl-/hydroxy- or alkoxy-functional siloxane mixture B in a molar ratio of alkyl groups according to A to fluoroalkyl groups according to B of from 99.9:0.1 to 0.1:99.9.

According to the invention, in particular an agent which contains from 0.9 to 3.6 mol of HCOOH or H$_3$CCOOH per mole of amino group in the silane co-oligomers, preferably from 1 to 1.1 mol of acid per mole of nitrogen of the amino functions, is used.

According to the invention, it is also possible to use an agent which, in addition to the silane co-oligomers according to formula I, contains from 0.001 to 0.2 mol of at least one alkoxysilane from the series consisting of tetraethoxysilane, methyltri-ethoxysilane, n-propyltriethoxysilane, isobutyltri-ethoxysilane, n-octyltriethoxysilane or isooctyltriethoxysilane, perfluoropropyltriethoxysilane or tridecafluoro-1,1,2,2-tetrahydrooctyltriethoxysilane, heptadecafluoro-1,1,2,2-tetrahydrodecyltriethoxysilane or corresponding hydrolysis products, partial hydrolysis products or the secondary reaction products thereof per mole of Si of the silane co-oligomers.

The present invention furthermore relates to substrates which are based on cellulose and/or starch, have water-repellent and simultaneously antifungal, antibacterial, insect-repellent and/or antialgal properties and obtainable by the process according to the invention.

The present, advantageous results are very important with regard to the use of wood in the indoor and outdoor area, in particular for subsequent use for construction elements comprising wood, for example windows, doors, facades, wooden floors, play grounds, elements for horticulture and landscaping and in hydraulic engineering and shipbuilding. In most applications, the timbers used are endangered by biological and climatic influences, in particular by wood-destroying and wood-discoloring fungi and molds. The chemical wood protection thus required may advantageously be provided by the present invention in the case of wood species which can be appropriately treated.

The present invention therefore also relates to articles which are based on at least one substrate obtainable by the process according to the invention or on a product thus treated.

The present invention is explained in more detail by the following examples without restricting the subject.

EXAMPLES

Vacuum pressure impregnations described in the examples were carried out by the following method: the wood samples to be impregnated were arranged in an impregnation vessel freely accessible to the impregnating liquid and weighed down with suitable weights. The impregnating liquid was then added so that the samples were completely covered. In a vacuum pressure vessel, a reduced pressure of about 100 mbar was applied and was maintained for the duration of 1 hour, after which a pressure of 12 bar was applied for the duration of 2 hours. The pressure was then reduced to atmospheric pressure.

Example 1

Effect on the Sorption Behavior

Samples of pine sapwood having the dimensions 5×10×30 mm were stored in a conditioning chamber at 20° C./65% relative humidity until the equilibrium moisture content had been reached and were impregnated by the vacuum pressure process with aqueous DYNASYLAN® HS 2909 with a dilution of (a) 33% (w/w) and (b) 10% (w/w) (DYNASYLAN® HS 2909 is a mixture of isobutyl-/3-aminopropyl-/hydroxy-siloxanes substantially neutralized with HCOOH). After removal from the impregnating liquid, the samples were dried for 4 hours at 60° C. and for a further 16 hours at 120° C. The samples were then stored in a conditioning chamber at 20° C./65% relative humidity and 20° C./91% relative humidity until the equilibrium moisture content according to DIN 52183 had been reached. The sorption behavior was not disadvantageously effected by the treatment (cf. FIG. 1).

Example 2

Reduction of the Water Uptake (Water-repellent Treatment)

Samples of pine sapwood having the dimensions 15×70× 100 mm were sealed on the cross-cut ends with a resilient sealing material and stored in a conditioning chamber at 20°

C./65% relative humidity until the equilibrium moisture content had been reached. The samples were treated by the vacuum pressure process with aqueous DYNASYLAN® HS 2909 with a dilution of (a) 33% (w/w) and (b) 10% (w/w) and (c) by the immersion process with a 33% (w/w) aqueous dilution of DYNASYLAN® HS 2909 and then heated for 16 hours at 60° C. The samples were completely immersed in tap water, and the water absorption was determined gravimetrically after 1 hour, 4 hours and 24 hours. As shown in FIG. 2, the water absorption of the treated samples was substantially reduced compared with the untreated control samples.

This example shows the very good water-repellent effect of the treatment with the agent used here.

Example 3

Increase of the Resistance to Brown Rot

Samples of pine sapwood having the dimensions 15×25×50 mm were stored in a conditioning chamber at 20° C./65% relative humidity until the equilibrium moisture content had been reached and were impregnated by the vacuum pressure process with aqueous DYNASYLAN® HS 2909 with a dilution of 33% (w/w). After removal from the impregnating liquid, the samples were dried for 4 hours at 60° C. and for a further 16 hours at 120° C. Thereafter, the samples were leached according to EN 84 and then tested for their durability with respect to the brown rot pathogens *Coniophora puteana* and *Gloeophyllum trabeum* according to EN 113. FIG. 3 shows the corrected mass loss according to EN 113. The treated samples showed high durability with respect to both brown rot fungi, while the untreated samples were considerably degraded.

This example shows the very good efficiency of the agent used here for protection from brown rot fungi.

Example 4

Increase of the Resistance to White Rot

Samples of beech wood having the dimensions 5×10×30 mm were stored in a conditioning chamber at 20° C./65% relative humidity until the equilibrium moisture content had been reached and were impregnated by the vacuum pressure process with aqueous DYNASYLAN® HS 2909 with a dilution of 33% (w/w). After removal from the impregnating liquid, the samples were dried for 4 hours at 60° C. and for a further 16 hours at 120° C. Thereafter, the samples were tested for their durability with respect to the white rot pathogen *Trametes versicolor* on the basis of EN 113. FIG. 4 shows the corrected mass loss after 12 weeks on the basis of EN 113. The treated samples showed high durability with respect to the white rot pathogen, while the untreated samples were considerably degraded.

This example shows the very good efficiency of the agent used here for protection from white rot fungi.

Example 5

Increase of the Resistance to Wood-discoloring Fungi and Molds

Samples of pine sapwood having the dimensions 15×70×270 mm were stored in a conditioning chamber at 20° C./65% relative humidity until the equilibrium moisture content had been reached. The samples were treated by the vacuum pressure process (a) with a water-repellent alkylalkoxysilane and (b) with aqueous DYNASYLAN® HS 2909 with a dilution of 33% (w/w) and then heated for 16 hours at 60° C. After storage for 2 weeks in a conditioning chamber at 20° C./65% relative humidity, the cross-cut ends were sealed with a resilient sealing material and the treated samples were exposed according to EN 927 on a weathering stand having a horizontal inclination of 45° in the open air. After weathering for one year, strong discolorations due to wood-discoloring fungi and molds were found on the backs of the untreated samples and of the samples treated according to a), while the samples treated according to b) were free of discolorations. FIG. 5 shows the backs of the samples.

This example shows the very good efficiency of the agent used here for protection from wood-discoloring fungi and molds.

Example 6

Increase in the Resistance to Insects (Termites)

Samples of pine sapwood having the dimensions 25×30×300 mm were stored in a conditioning chamber at 20° C./65% relative humidity until the equilibrium moisture content had been reached and were then impregnated with an aqueous solution consisting of ⅓ DYNASYLAN® HS 2909 and ⅔ tap water, by the vacuum pressure process. After removal from the impregnating liquid, the samples were dried for 4 hours at 60° C. and for a further 16 hours at 120° C. The samples were exposed in an active termite field in Peroguarda (southern Portugal). After an exposure time of 6 months, in some cases substantial degradation by termites and the occurrence of living termites were observed on untreated samples, while the treated samples had only very slight isolated degradation and no living termites were observed.

This example shows the very good efficiency of the agent used here for protection from insects.

Example 7

Improvement of the Surface Hardness

Samples of beech wood having the dimensions 4×50×50 mm were stored in a conditioning chamber at 20° C./65% relative humidity until the equilibrium moisture content had been reached and were then impregnated by the vacuum pressure process with DYNASYLAN® HS 2909. After removal from the impregnating liquid, the samples were dried for 4 hours at 60° C. and for a further 16 hours at 120° C. Thereafter, the samples were stored in a conditioning chamber at 20° C./65% relative humidity until the equilibrium moisture content had been reached. The testing of the Brinell surface hardness according to EN 1534 at a test force of 1000 N gave 36.7 N/mm$^2$ for the samples treated in this manner and 25.0 N/mm$^2$ for untreated samples.

This example shows the very good suitability of the agent used here for increasing the surface hardness.

Example 8

Protection of Active Substances from Leaching

Samples of pine sapwood having the dimensions 5×10×30 mm were stored in a conditioning chamber at 20° C./65% relative humidity until the equilibrium moisture content had been reached. The samples were impregnated with a solution consisting of (a) 3% of boric acid, 33% of DYNASYLAN® HS 2909 and 64% of water or (b) 3% of boric acid and 97% of water by the vacuum process. After removal from the impregnating liquid, the samples were dried for 4 hours at 60° C. and for a further 16 hours at 120° C. and then stored for 24 hours in the conditioning chamber at 20° C./65% relative humidity. In each case 5 samples were completely covered with 37.5 ml of demineralized water and thoroughly impregnated with the aid of a reduced pressure of 100 mbar and then remained in the water at atmospheric pressure for 4 days. The analysis of the water samples taken from the vessels gave a boron content of 0.3 g/l in the case of the samples treated according to (a) and of 0.6 g/l in the case of the samples treated according to (b).

This example shows the very good suitability of the agent used here for protecting active substances from leaching.

Example 9

UV Protection

Samples of pine sapwood having the dimensions 15×70×270 mm were stored in a conditioning chamber at 20° C./65% relative humidity until the equilibrium moisture content had been reached. The samples were impregnated by the vacuum pressure process with a 3% (w/w) aqueous solution of the free radical scavenger CGL 1198 (CIBA) and then dried for 3 days at 20° C./65% relative humidity, for 1 day at 30° C., for 1 day at 40° C., for 1 day at 50° C. and for 1 day at 60° C. 2.5 mol of water containing hydrochloric acid (pH 1.5) were added to one mole of DYNASYLAN® IBTEO, and the mixture was stirred until it became clear. 3% (w/w) of Tinuvin 384 (CIBA) were added to the hydrolysis product thus prepared and stirring was effected for 15 minutes. The wood samples were immersed therein completely for 15 minutes and then dried for one day at 20° C./65% relative humidity and for 1 hour at 60° C. Thereafter, the samples were completely immersed in F 8815 for 15 minutes and then dried for one day at 20° C./65% relative humidity and for 1 hour at 60° C. The samples were exposed to weathering for two weeks in the QUV accelerated weathering apparatus with cyclic exposure with UV(A) radiation and spraying according to EN 927-6. After the weathering, the treated samples were substantially less discolored than the untreated samples.

This example shows the very good efficiency of the agent used here for protection from UV radiation.

Example 10

Ensuring Coatability

Samples of pine sapwood having the dimensions 15×75×300 mm were stored in a conditioning chamber at 20° C. and 65% relative humidity until the equilibrium moisture content had been reached and were then impregnated with an aqueous solution consisting of 1/6 DYNASYLAN® HS 2909 and 5/6 tap water by the vacuum pressure process. After removal from the impregnating liquid, the samples were dried for 48 hours at 110° C. The treated samples were coated with commercial wood finishes (manufacturer: Akzo Nobel) by brushing:

a) application of three coats of Cetol WF 760 (water-borne transparent acrylic system), total film thickness: 90 μm b) priming with Cetol WP 560 and top coating of Cetol WF 780 (water-borne transparent acrylic systems), total film thickness: 120 μm c) application of two coats of Rubbol WF 350 (water-borne covering acrylic system)

The coated samples were stored for 2 weeks at 20° C. and 65% relative humidity and then subjected to a coat adhesion test based on DIN EN ISO 4624 using a PosiTest® Adhesion Tester (DeFelsko Corporation Ogdensburg, N.Y.). The following median values were obtained for the coat adhesion from three measurements in each case:

|  | Variant a) | Variant b) | Variant c) |
|---|---|---|---|
| Untreated | 0.69 MPa | 1.59 MPa | 0.69 MPa |
| Treated | 0.97 MPa | 1.73 MPa | 1.11 MPa |

Table for example 10:
Coat adhesion on untreated pine sapwood and pine sapwood treated according to the invention, based on DIN EN ISO 4624.

It is clearly evident that the coat adhesion was not adversely affected by the treatment according to the invention.

Example 11

Fire Protection

Samples of pine sapwood having the dimensions 5×10×100 mm were stored in a conditioning chamber at 20° C. and 65% relative humidity until the equilibrium moisture content had been reached and were impregnated by the vacuum pressure process with DYNASYLAN® HS 2909. After removal from the impregnating liquid, the samples were dried for 4 hours at 60° C. and for a further 16 hours at 120° C. Thereafter, the samples were stored in a conditioning chamber at 20° C. and 65% relative humidity until the equilibrium moisture content had been reached. In each case the treated and untreated samples were then arranged in a V shape at an angle of about 45° to the horizontal, the spacing at the lowest point being 5 mm. The control and the treated sample were ignited at the same time with a Bunsen burner for 25 seconds. When ⅔ of the untreated sample had been burned, the flame was extinguished. The combustion zone of the treated wood sample was compared with the untreated piece of wood.

The combustion zone of the treated samples was on average 36 mm, while 66 mm of the untreated sample had burned. This shows that the wood was provided with fire-retardant properties by the treatment according to the invention.

What is claimed is:

1. A method for the treatment of wood or wood products, comprising:
   impregnating the wood or wood products with a treatment agent under a vacuum pressure of 1.5 to 20 bar, wherein the treatment agent comprises:
   5 to 99.5% by mass water;
   less than 95% by weight of an alcohol;
   at least one linear, cyclic, branched or crosslinked co-oligomer of the formula (I) comprising at least one siloxane structure selected from the group consisting of an alkyl-siloxane, an aminoalkyl-siloxane, an alkoxy-siloxane, and a hydroxy-siloxane:

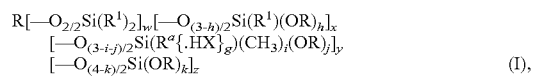

(I), wherein
each R is independently H, methyl, ethyl, isopropyl or n-propyl,
each $R^1$ is independently a linear, branched or cyclic, optionally substituted alkyl group having 1 to 18 carbon atoms,
each $R^a$ is an aminoalkyl group of the formula (Ia):

(Ia), wherein $0 \leq d \leq 6$, $0 \leq f \leq 6$, where e equals 0, if d equals 0, then β equals 1, where e equals 1, if d>0, then β equals 1 or 2, X is independently at least one of an organic or inorganic acid radical selected from the group consisting of chloride, formate, acetate and phosphate, g equals 0, 1, 2 or 3, h, i and j, independently are 0 or 1, k is 0, 1, 2 or 3 and x, y, z and w are identical or different and x is a number of from 0 to 50, y is a number of from 1 to 50, z is a number of from 0.001 to 10 and w is a number of from 0 to 30, with $(w+x+z)>1$; and from 0.001 to 0.2 mol of at least one alkoxysilane selected from the group consisting of tetraethoxysilane, methyltriethoxysilane, n-propyltriethoxysilane, isobutyltriethoxysilane, n-octyltriethoxysilane, isooctyltriethoxysilane, perfluoropropyltriethoxysilane, tridecafluoro-1,1,2,2-tetrahydrooctyltriethoxysilane, corresponding hydrolysis products, and partial hydrolysis products per mole of Si of the siloxane co-oligomers;

wherein the treated wood or wood product is water-repellent and simultaneously has at least one property selected from the group consisting of an antifungal, antibacterial, insect-repellent and antialgal property; and a content of free acid in the treatment agent is less than 10% by mass, based on the composition of the agent, wherein the impregnated wood or wood product is dried under controlled conditions in the open air until a wood moisture content of from 12 to 18% is established and is then (i) treated for from 2 hours to 4 weeks at from 50 to 120° C. or (ii) dried for from 2 hours to 4 weeks at from about 50 to 60° C. and optionally after treated for further 2 to 48 hours at about 120° C. or (iii) drying in a conditioning chamber or drying with superheated steam is carried out for from 2 hours to 2 weeks at from about 50 to 130° C.

2. The method according to claim 1, wherein a content of the co-oligomer of the formula I is from 0.5 to 95% by mass, based on the mass of the treatment agent.

3. The method according to claim 1, wherein $R^1$ comprises an alkyl group and a fluoroalkyl group.

4. The method according to claim 3, wherein a proportion of the fluoroalkyl group is from 0.001 to 99.999 mol %, based on all alkyl groups $R^1$ according to the formula I.

5. The method of claim 3, wherein the treatment agent comprises from 0.5 to 95% by mass of a mixture of siloxane co-oligomers according to formula I, based on the composition of the agent, and the preparation of the siloxane oligomer mixture is based on a molar ratio of a aminoalkylsilyl group to a fluoroalkylalkoxysilane of from 3:1 to 1:3.33.

6. The method of claim 5, wherein from 0.001 to 99.999 mol % of the fluoroalkylalkoxysilane is replaced by a corresponding molar amount of at least one of a alkylalkoxysilane and tetraalkoxysilane in the preparation of the siloxanes oligomer mixture.

7. The process according to claim 1 further comprising:
impregnating the wood or wood product as a vacuum pressure impregnation;
allowing the treatment agent to act; and
drying.

8. The process as claimed in claim 7, wherein the entire wood sample is penetrated by the treatment agent.

9. The process as claimed in claim 1, further comprising:
subjecting the wood or wood product to a vacuum pressure of from 10 to 500 mbar in a pressure-resistant impregnation reactor for from 5 minutes to 8 hours before the impregnation;
maintaining the pressure of from 10 to 500 mbar and immersing or covering the wood or wood product with the treatment agent;
and
increasing the pressure to 1.5 to 20 bar for from 0.5 to 4 hours.

10. A method for protecting wood or wood products from the effects due to a fungus, comprising:
impregnating the wood and wood products according to the method of claim 1 with an effective amount of the treatment agent.

11. The method of claim 10, wherein the fungus is basidiomycetes.

12. The method of claim 1, wherein the treatment agent comprises from 0.5 to 95% by mass of a mixture of siloxane co-oligomers according to the formula I, based on the composition of the agent, and the preparation of the siloxane oligomer mixture is based on a molar ratio of an aminoalkylsilyl group to an alkylsilyl group of from 4:1 to 1:4.

13. The method of claim 12, wherein the agent comprises from 0.5 to 95% by mass of a mixture of siloxane co-oligomers according to formula I, based on the composition of the treatment agent, and wherein from 0.001 to 55 mol % of the alkylsilyl group is replaced by a corresponding molar amount of at least one further alkylsilyl group and/or tetraalkoxysilane in the preparation of the siloxane oligomer mixture.

14. The method of claim 1, wherein the treatment agent comprises from 0.5 to 95% by mass of a mixture of siloxane co-oligomers according to formula I, based on the composition of the treatment agent, and the siloxane co-oligomer mixture is prepared by mixing an aminoalkyl-/alkyl-/hydroxy- or alkoxy-functional siloxane mixture A with an aminoalkyl-/fluoroalkyl-/hydroxy- or alkoxy-functional siloxane mixture B in a molar ratio of alkyl groups according to A to fluoroalkyl groups according to B of from 99.9:0.1 to 0.1:99.9.

15. The method of claim 1, wherein the treatment agent comprises an aminoalkyl-siloxane and further comprises from 0.9 to 3.6 mol of HCOOH or $H_3CCOOH$ per mole of the amino group in the siloxane co-oligomers.

16. The method for treatment of wood or wood products according to claim 1, wherein the treatment provides at least one effect selected from the group of effects consisting of hardening the wood or wood product, protection of the wood or wood product from UV radiation and improving the fire resistance of the wood or wood product.

* * * * *